United States Patent [19]

Stähle et al.

[11] 4,100,292
[45] Jul. 11, 1978

[54] 2-[N-PHENYL-N-(CYCLOALKYL-METHYL)-AMINO]-2-IMIDAZOLINES AND SALTS THEREOF

[75] Inventors: Helmut Stähle; Herbert Köppe; Werner Kummer, all of Ingelheim am Rhein; Klaus Stockhaus, Bingen am Rhein; Wolfgang Hoefke, Budenheim; Franz Josef Köhn, Bingen am Rhein, all of Fed. Rep. of Germany

[73] Assignee: Boehringer Ingelheim GmbH, Ingelheim am Rhein, Fed. Rep. of Germany

[21] Appl. No.: 824,044

[22] Filed: Aug. 12, 1977

[30] Foreign Application Priority Data

Aug. 14, 1976 [DE] Fed. Rep. of Germany ....... 2636732

[51] Int. Cl.² .............. C07D 233/50; A61K 31/415
[52] U.S. Cl. ................ 424/273 R; 548/315; 548/351
[58] Field of Search .......................... 548/351; 424/273

[56] References Cited

U.S. PATENT DOCUMENTS

| 3,202,660 | 8/1965 | Zeile et al. ............. 548/351 |
| 3,740,401 | 6/1973 | Stähle et al. ............ 548/351 |
| 3,752,810 | 8/1973 | Stähle et al. ............ 548/351 |
| 3,850,926 | 11/1974 | Stähle et al. ........... 548/351 |

OTHER PUBLICATIONS

Stäehle et al., Chem. Abst. 1974, vol. 81, No. 63628d.
Stäehle et al., Chem. Abst., 1974, vol. 81, No. 169545.

*Primary Examiner*—Natalie Trousof
*Attorney, Agent, or Firm*—Hammond & Littell

[57] ABSTRACT

Compounds of the formula

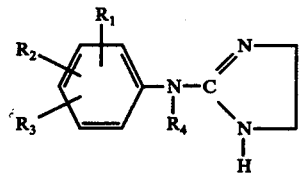

wherein
$R_1$, $R_2$ and $R_3$, which may be identical or different from each other, are each hydrogen, fluorine, chlorine, bromine, methyl, ethyl, methoxy, hydroxyl, trifluoromethyl or cyano; and
$R_4$ is (cycloalkyl of 3 to 6 carbon atoms)-methyl; and non-toxic, pharmacologically acceptable acid addition salts thereof. The compounds as well as their salts are useful as analgesics.

4 Claims, No Drawings

2-[N-PHENYL-N-(CYCLOALKYL-METHYL)-AMINO]-2-IMIDAZOLINES AND SALTS THEREOF

This invention relates to novel 2-[N-phenyl-N-(cycloalkyl-methyl)-amino]-2-imidazolines and acid addition salts thereof, as well as to methods of preparing these compounds.

More particularly, the present invention relates to a novel class of 2-phenylamino-2-imidazolines represented by the formula

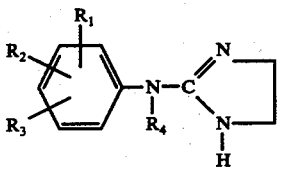

wherein
$R_1$, $R_2$ and $R_3$, which may be identical or different from each other, are each hydrogen, fluorine, chlorine, bromine, methyl, ethyl, methoxy, hydroxyl, trifluoromethyl or cyano; and $R_4$ is (cycloalkyl of 3 to 6 carbon atoms)-methyl; and non-toxic, pharmacologically acceptable acid addition salts thereof.

The compounds embraced by formula I may be prepared by the following methods:

Method A

By reacting a 2-phenylimino-2-imidazolidine of the formula

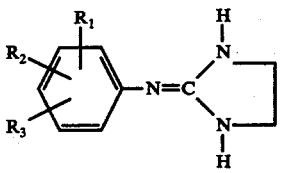

wherein $R_1$, $R_2$ and $R_3$ have the same meanings as in formula I, with a cycloalkyl-methyl halide of the formula

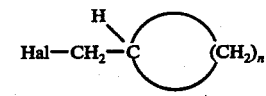

wherein
Hal is chlorine, bromine or iodine, and
$n$ is 2, 3, 4 or 5

The reaction is carried out by heating a mixture of the reactants, preferably in the presence of a polar or non-polar organic solvent, to a temperature between about 50° and 150° C. The specific reaction conditions depend largely upon the reactivity of the reaction partners. The cycloalkylmethyl halide reactant is advantageously provided in excess over the stoichiometrically required amount, and the reaction is preferably performed in the presence of an acid-binding agent.

Method B

By reacting a compound of the formula

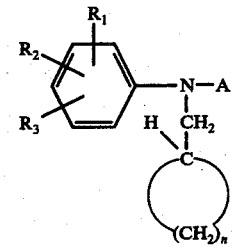

wherein
$R_1$, $R_2$ and $R_3$ have the same meanings as in formula I;
$n$ has the same meanings as in formula III; and
A is cyano or

wherein Y is alkoxy of 1 to 4 carbon atoms;
alkylthio of 1 to 4 carbon atoms,
sulfhydril or amino;
with ethylenediamine or an acid addition salt thereof.

The reaction is carried out at a temperature between 60° and 80° C. The presence of a solvent is not required. It is advantageous to provide the ethylenediamine reactant in excess over the stoichiometrically required amount.

In the alkylation reaction pursuant to method A the cycloalkyl-methyl substitution takes place exclusively on the bridge nitrogen atom of the 2-phenylimino-imidazolidine. The structure of the end product of method B is fixed by virtue of the synthesis. In either case, the position of the substituents can also be ascertained by NMR-spectroscopy [of H. Stähle et al., Liebigs Ann. Chem. 751, 159 et seq. (1971)].

The starting compounds of the formula II are disclosed in Belgian Pat. Nos. 623,305; 687,657; and 705,944.

The starting compounds of the formula III may be prepared by halogenation of the corresponding primary alcohols.

The starting compounds of the formula IV may be obtained by reacting a corresponding aniline with a cycloalkylmethyl halide of the formula III, followed by reaction of the resulting secondary amine with a cyanate or thiocyanate, whereby a corresponding urea or thiourea is formed. The urea or thiourea can then be further reacted with an alkylating agent to form a corresponding isouronium salt or isothiouronium salt, from which the corresponding isourea or isothiourea can be formed with a base. Dehydration of a urea compound or splitting off $SH_2$ from a thiourea compound with a lead salt or mercury salt leads to the corresponding cyanamide which can then be converted into the corresponding guanidine by the addition of ammonia thereto.

The compounds embraced by formula I are organic bases and therefore form acid addition salts with inorganic or organic acids. Examples of non-toxic, pharmacologically acceptable acid addition salts are those formed with hydrochloric acid, hydrobromic acid, hydroiodic acid, hydrofluoric acid, sulfuric acid, phosphoric acid, nitric acid, acetic acid, propionic acid, butyric acid, caproic acid, valeric acid, oxalic acid, malonic acid, succinic acid, maleic acid, fumaric acid, lactic acid, tartaric acid, citric acid, malic acid, benzoic acid, p-hydroxy-benzoic acid, p-amino-benzoic acid, phthalic acid, cinnamic acid, salicylic acid, ascorbic acid, methanesulfonic acid, 8-chlorotheophylline or the like.

The following examples illustrate the present invention and will enable others skilled in the art to understand it more completely. It should be understood, however, that the invention is not limited solely to the particular examples given below.

EXAMPLE 1

2-[N-(cyclopropyl-methyl)-N-(2,6-dichloro-phenyl)-amino]-2-imidazoline by method A A mixture consisting of 6.9 gm (0.03 mol) of 2-(2,6-dichlorophenyl-imino)-imidazolidine, 2.9 gm (110% of stoichiometrically required amount) or chloromethyl-cyclopropane, 4 gm of sodium carbonate and 50 ml of absolute toluene was refluxed for 32 hours, while stirring. Thereafter, the reaction solution was evaporated to dryness in vacuo, and the residue was dissolved in about 1N hydrochloric acid. The resulting acidic solution was extracted several times with ether, and the ethereal extracts were discarded. The acidic aqueous phase was then fractionally extrated with ether at stepwisely increasing pH-values (alkalization with dilute sodium hydroxide), and the thin-layer chromatographically pure fractions were combined, dried over magnesium sulfate and evaporated in vacuo, yielding as the residue 0.9 gm (10.6% of theory) of the compound of the formula

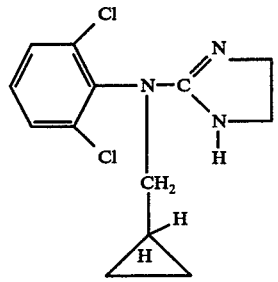

which had a melting point of 126°–129° C.

EXAMPLE 2

2-[N-(Cyclopropyl-methyl)-N-(2-fluoro-6-trifluoromethylphenyl)-amino]-2-imidazoline by method A A mixture consisting of 8 gm (0.032 mol) of 2-[(2-fluoro-6-trifluoromethyl-phenyl)-imino]-imidazolidine, 4.6 gm (105% of the stoichiometrically required amount), 5 cc of trimethylamine acid 25 ml of absolute toluene was heated at 120° C for 18 hours in a closed tube. After cooling, the liquid phase was decanted, the solid residue was dissolved in about 150 cc of 1N hydrochloric acid, the solution was extracted several times with ether, and the ethereal extracts were discarded. The acidic aqueous phase and fractionally extracted with ether at stepwisely increasing pH-values (alkalization with dilute sodium hydroxide). The thin-layer chromatographically uniform fractions were combined, dried over Drierite (calcium sulfate) and evaporated to dryness in vacuo. The residue was caused to crystallize by stirring it with petroleum ether, the mixture was suction-filtered, and the filter cake was dried, yielding 5.7 gm (58.4% of theory) of 2-[N-(cyclopropyl-methyl)-N-(2-fluoro-6-trifluoromethyl-phenyl)-amino]-2-imidazoline, m.p. 126°–127° C.

Using procedures analogous to those described in Examples 1 and 2, the compounds shown in the following table were also prepared.

Table $$A-N(B)-C(=N\cdots)(N-H\cdots)$$ (2-imidazoline ring)

| Ex. | A | B | m.p. °C | Yield % of theory |
|---|---|---|---|---|
| 3 | 2,6-diCl-phenyl | cyclohexyl-CH$_2$– | 140–141 | 49.5 |
| 4 | 2,6-diCl-phenyl | cyclopentyl-CH$_2$– | 155–157 | 27.8 |
| 5 | 2,6-diCl-phenyl | cyclobutyl-CH$_2$– | 155–158 | 8.4 |
| 6 | 2,6-diBr-phenyl | cyclohexyl-CH$_2$– | 158–158 | 31.9 |
| 7 | 2-Cl-6-F-phenyl | cyclopropyl-CH$_2$– | 116–118 | 28.0 |
| 8 | 2,6-diCl-4-Br-phenyl | cyclopropyl-CH$_2$– | 143–145 | 27.5 |
| 9 | 2-Cl-6-CH$_3$-phenyl | cyclopropyl-CH$_2$– | 127–128 | 30.3 |
| 10 | 2-Cl-6-CH$_3$-phenyl | cyclopentyl-CH$_2$– | 134–136 | 18.0 |
| 11 | 3-CH$_3$-5-F-phenyl | cyclohexyl-CH$_2$– | 101–103 | 25.3 |
| 12 | 2,4-diCl-phenyl | cyclohexyl-CH$_2$– | 146–148 | 17.9 |
| 13 | 2,3-diCl-phenyl | cyclohexyl-CH$_2$– | 132–134 | 9.7 |
| 14 | 2-CH$_3$-3-Cl-phenyl | cyclohexyl-CH$_2$– | 114–116 | 20.2 |

Table-continued $$A-N-C\begin{smallmatrix}N\\\|\\N\\|\\H\end{smallmatrix}$$

| Ex. | A | B | m.p. °C | Yield % of theory |
|---|---|---|---|---|
| 15 | 2-Cl, 4-F-phenyl | phenyl-CH$_2$- | 131–132 | 26.9 |
| 16 | 2-Cl, 4-CH$_3$-phenyl | phenyl-CH$_2$- | 149–150 | 16.6 |
| 17 | phenyl | cyclopropyl-CH$_2$- | oil | 49.5 |
| 18 | 2-Br, 3-CH$_3$-phenyl | cyclopropyl-CH$_2$- | 105–106 | 23.2 |
| 19 | 2-C$_2$H$_5$, 3-C$_2$H$_5$-phenyl | cyclopropyl-CH$_2$- | 145–147 | 29.7 |
| 20 | 2-Br, 3-Br-phenyl | cyclopropyl-CH$_2$- | 145–147 | 29.5 |
| 21 | 2-OCH$_3$, 4-CH$_3$O-phenyl | cyclopropyl-CH$_2$- | 99–101 | 29.0 |
| 22 | 4-NC-phenyl | cyclopropyl-CH$_2$- | 115–117 | 18.0 |
| 23 | 2-Br, 3-Br-phenyl | phenyl-CH$_2$- | 168–171 | 20.7 |
| 24 | 2-Br, 3-Br-phenyl | cyclopentyl-CH$_2$- | 151–153 | 7.5 |
| 25 | 2-Br, 3-Br, 5-Br-phenyl | cyclopropyl-CH$_2$- | 110–111 | 41.1 |
| 26 | 2-Br, 4-Br-phenyl | cyclopropyl-CH$_2$- | 161–163 | 20.6 |
| 27 | 2-Br, 3-Br-phenyl | cyclopropyl-CH$_2$- | 88–89 | 4.4 |
| 28 | 2-Br, 4-Cl-phenyl | cyclopropyl-CH$_2$- | 153–155 | 7.6 |
| 29 | 2-Br, 4-F-phenyl | cyclopropyl-CH$_2$- | 114 | 20.3 |
| 30 | 2-CF$_3$, 4-Cl-phenyl | cyclopropyl-CH$_2$- | 111 | 14.2 |
| 31 | 2-Br, 3-Br-phenyl | cyclopropyl-CH$_2$- | 99–102 | 16.4 |

The compounds of this invention, that is, those embraced by formula I and their non-toxic, pharmacologically acceptable acid addition salts, have useful pharmacodynamic properties. More particularly, they exhibit analgesic activity in warm-blooded animals, such as mice, and are therefore useful for the relief of pain due to migraine or the like.

The analgesic activity of the compounds of the present invention was ascertained in mice by standard test methods for analgesia, namely with writhing test [Blumberg et al., Proc. Soc. Exp. Biol. Med. 118, 763 (1965)] and the hotplate test [Woolfe et al., J. Pharmacol. Exp. Ther. 80, 300 (1944)]. The results of these tests showed that the novel 2-[N-(cycloalkyl-methyl)-N-phenyl-amine]-2-imidazolines of the present invention are up to 100 times more effective analgesics than morphine and the N-allyl-2-phenylamine-2-imidazolines disclosed in German Offenlegungsschrift No. 1,958,201.

In addition, the compounds of the formula I and their non-toxic acid addition salts, especially those where $R_4$ is cyclopropylmethyl or cyclobutylmethyl, exhibit very strong bradicardiac activity in warm-blooded animals, such as rabbits and cats, and are therefore useful for the treatment of coronary disorders.

For pharmaceutical purposes the compounds according to the present invention are administered to warm-blooded animals perorally, parenterally or rectally as active ingredients in customary dosage unit compositions, that is, compositions in dosage unit form consisting essentially of an inert pharmaceutical carrier and one effective dosage unit of the active ingredient, such as tablets, coated pills, capsules, wafers, powders, solutions, suspensions, emulsions, syrups, suppositories and the like. One effective dosage unit of the compounds according to the present invention is from 0.016 to 1.34 mgm/kg body weight, preferably 0.016 to 0.5 mgm/kg body weight.

The following examples illustrate a few pharamaceutical dosage unit compositions comprising a compound of the present invention as an active ingredient and represent the best modes contemplated of putting the invention into practical use. The parts are parts by weight unless otherwise specified.

EXAMPLE 32

Coated tablets

The tablet core composition is compounded from the following ingredients:

| | | |
|---|---|---|
| 2-[N-(2,6-Dichloro-phenyl)-N-(cyclo-propyl-methyl-amino]-2-imidazoline | 5 | parts |
| Lactose | 65 | " |
| Corn starch | 130 | " |
| Sec. calcium phosphate | 40 | " |
| Soluble starch | 3 | " |
| Magnesium stearate | 3 | " |
| Colloidal silicic acid | 4 | " |
| Total | 250 | parts |

Preparation:

The active ingredient is admixed with part of the excipients, the mixture is kneaded thoroughly with an aqueous solution of the soluble starch, and the moist mass is granulated with the aid of a screen in the conventional way. The dried granulate is admixed with the remaining excipients and the composition is compressed into 250 mg-tablet cores which are then coated in the usual way with a mixture consisting essentially of sugar, talcum and gum arabic. Each coated tablet is an oral dosage unit composition containing 5 mgm of the active ingredient.

EXAMPLE 33

Hypodermic solution

The solution is compounded from the following ingredients:

| | | |
|---|---|---|
| 2-[N-(2,6-Dichloro-phenyl)-N-(cyclo-propyl-methyl)-amino]-2-imidazoline | 0.02 | parts |
| Methyl-p]hydroxy-benzoate | 0.07 | " |
| Propyl-p-hydroxy-benzoate | 0.03 | " |
| Demineralized water q.s. ad | 100 | " |
| | | by vol. |

Preparation:

The active ingredient and the p-hydroxy-benzoates are dissolved in the demineralized water, and the solution is filtered. 5 ml (20 drops) of the filtrate are an oral dosage unit composition containing 1 mgm of the active ingredient.

Any one of the other compounds embraced by formula I or a non-toxic, pharmacologically acceptable acid addition salt thereof may be substituted for the particular active ingredient in Examples 32 through 34. Likewise, the amount of active ingredient in these illustrative examples may be varied to achieve the dosage unit range set forth above, and the amounts and nature of the inert pharmaceutical carrier ingredients may be varied to meet particular requirements.

While the present invention has been illustrated with the aid of certain specific embodiments thereof, it will be readily apparent to others skilled in the art that the invention is not limited to these particular embodiments, and that various changes and modifications may be made without departing from the spirit of the invention or the scope of the appended claims.

We claim:

1. A compound of the formula

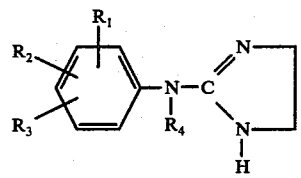

wherein $R_1$, $R_2$ and $R_3$ are hydrogen, fluorine, chlorine, bromine, methyl, ethyl, methoxy, trifluoromethyl or cyano; and $R_4$ is (cycloalkyl of 3 to 6 carbon atoms)-methyl; and non-toxic, pharmacologically acceptable acid addition salts thereof.

2. A compound of claim 1, which is 2-[N-(2,6-dichloro-phenyl)-N-(cyclopropyl-methyl)-amino]-2-imidazoline or a non-toxic, pharmacologically acceptable acid addition salt thereof.

3. An analgesic pharmaceutical dosage unit composition consisting essentially of an inert pharmaceutical carrier and an effective analgesic amount of a compound of claim 1.

4. The method of relieving pain in a warm-blooded animal, which comprises perorally, parenterally or rectally administering to said animal an effective analgesic amount of a compound of claim 1.

* * * * *